(12) United States Patent
Weeber et al.

(10) Patent No.: US 12,204,178 B2
(45) Date of Patent: Jan. 21, 2025

(54) DIFFRACTIVE LENSES FOR PRESBYOPIA TREATMENT

(71) Applicant: AMO Groningen B.V., Groningen (NL)

(72) Inventors: Hendrik A. Weeber, Groningen (NL); Robert Rosen, Groningen (NL)

(73) Assignee: AMO Groningen B.V., Groningen (NL)

(*) Notice: Subject to any disclaimer, the term of this patent is extended or adjusted under 35 U.S.C. 154(b) by 604 days.

(21) Appl. No.: 17/057,637

(22) PCT Filed: Dec. 4, 2019

(86) PCT No.: PCT/EP2019/083615
§ 371 (c)(1),
(2) Date: Nov. 20, 2020

(87) PCT Pub. No.: WO2020/115104
PCT Pub. Date: Jun. 11, 2020

(65) Prior Publication Data
US 2021/0294123 A1    Sep. 23, 2021

Related U.S. Application Data

(60) Provisional application No. 62/776,362, filed on Dec. 6, 2018.

(51) Int. Cl.
G02C 7/04 (2006.01)
A61F 2/16 (2006.01)

(52) U.S. Cl.
CPC ............ G02C 7/044 (2013.01); *A61F 2/1656* (2013.01); *G02C 2202/20* (2013.01)

(58) Field of Classification Search
CPC ....................................................... G02C 7/044
(Continued)

(56) References Cited

U.S. PATENT DOCUMENTS 3,367,734 A    2/1968   Karl et al.
3,722,986 A    3/1973   Tagnon
(Continued)

FOREIGN PATENT DOCUMENTS

AU    2005230194 B2    12/2010
CA       2501217 A1     4/2004
(Continued)

OTHER PUBLICATIONS

International Search Report and Written Opinion for Application No. PCT/EP2019/083615, mailed on Mar. 17, 2020, 14 pages.
(Continued)

*Primary Examiner* — James R Greece

(57) ABSTRACT

Apparatuses, systems and methods for providing improved ophthalmic lenses, particularly intraocular lenses (IOLs), include features for reducing dysphotopsia effects, such as haloes and glare, in extended range of vision lenses. Exemplary ophthalmic lenses can include an optic including a first surface and a second surface each disposed about an optical axis and extending radially outward from the optical axis to an outer periphery of the optic. A diffractive profile including a plurality of echelettes is disposed on the first surface such that no echelette on the first surface repeats between the optical axis and the outer periphery of the optic.

33 Claims, 8 Drawing Sheets

(58) Field of Classification Search
USPC .................................................. 351/159.44
See application file for complete search history.

(56) References Cited

U.S. PATENT DOCUMENTS

| | | | |
|---|---|---|---|
| 4,210,391 A | 7/1980 | Cohen et al. |
| 4,340,283 A | 7/1982 | Cohen |
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,856,234 A | 8/1989 | Goins |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,932,970 A | 6/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,016,977 A | 5/1991 | Baude et al. |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,066,301 A | 11/1991 | Wiley |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,161,057 A | 11/1992 | Johnson |
| 5,173,723 A | 12/1992 | Volk et al. |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,260,727 A | 11/1993 | Oksman et al. |
| 5,322,649 A | 6/1994 | Rheinish et al. |
| 5,344,447 A | 9/1994 | Swanson |
| 5,349,394 A | 9/1994 | Freeman et al. |
| 5,349,471 A | 9/1994 | Morris et al. |
| 5,381,190 A | 1/1995 | Rehse et al. |
| 5,384,606 A | 1/1995 | Koch et al. |
| 5,408,281 A | 4/1995 | Zhang |
| 5,443,506 A | 8/1995 | Garabet |
| 5,443,507 A | 8/1995 | Jacobi |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,684,595 A | 11/1997 | Kato et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,094 A | 10/1999 | Werblin et al. |
| 5,968,095 A | 10/1999 | Norrby |
| 5,982,543 A | 11/1999 | Fiala |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,126,283 A | 10/2000 | Wen et al. |
| 6,126,286 A | 10/2000 | Portney |
| 6,139,145 A | 10/2000 | Israel |
| 6,142,625 A | 11/2000 | Sawano et al. |
| 6,145,987 A | 11/2000 | Baude et al. |
| 6,154,323 A | 11/2000 | Kamo |
| 6,199,986 B1 | 3/2001 | Williams et al. |
| 6,210,005 B1 | 4/2001 | Portney |
| 6,215,096 B1 | 4/2001 | Von Wallfeld et al. |
| 6,224,211 B1 | 5/2001 | Gordon |
| 6,231,603 B1 | 5/2001 | Lang et al. |
| 6,270,220 B1 | 8/2001 | Keren |
| 6,271,915 B1 | 8/2001 | Frey et al. |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,462,874 B1 | 10/2002 | Soskind |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,511,180 B2 | 1/2003 | Guirao et al. |
| 6,520,638 B1 | 2/2003 | Roffman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,391 B2 | 4/2003 | Ross, III et al. |
| 6,547,822 B1 | 4/2003 | Lang |

(56) References Cited

U.S. PATENT DOCUMENTS

| | | |
|---|---|---|
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De Carle |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van Heugten |
| 9,335,563 B2 | 5/2016 | Weeber |
| 9,335,564 B2 | 5/2016 | Choi et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 2001/0018612 A1 | 8/2001 | Carson et al. |
| 2002/0082690 A1 | 6/2002 | Sarbadhikari |
| 2002/0093701 A1 | 7/2002 | Zhang et al. |
| 2002/0118337 A1 | 8/2002 | Perrott et al. |
| 2003/0014107 A1 | 1/2003 | Reynard |
| 2003/0076478 A1 | 4/2003 | Cox |
| 2003/0169491 A1 | 9/2003 | Bender et al. |
| 2003/0171808 A1 | 9/2003 | Phillips |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0189981 A1 | 9/2004 | Ross et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0238702 A1 | 10/2006 | Glick et al. |
| 2006/0244904 A1 | 11/2006 | Hong et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0258143 A1 | 11/2007 | Portney |

(56) References Cited

U.S. PATENT DOCUMENTS

| | | |
|---|---|---|
| 2007/0268451 A1 | 11/2007 | Raghuprasad |
| 2007/0282438 A1 | 12/2007 | Hong et al. |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0240328 A1 | 9/2009 | Treushnikov et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0057202 A1 | 3/2010 | Bogaert |
| 2010/0087921 A1 | 4/2010 | Simpson |
| 2010/0131060 A1 | 5/2010 | Simpson et al. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2011/0022170 A1 | 1/2011 | Simpson et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0270596 A1 | 11/2011 | Weeber |
| 2011/0313522 A1 | 12/2011 | Hayes |
| 2011/0313523 A1 | 12/2011 | Hayes |
| 2011/0313525 A1 | 12/2011 | Cumming |
| 2012/0059464 A1 | 3/2012 | Zhao |
| 2012/0140166 A1* | 6/2012 | Zhao .................. G02C 7/041 351/159.44 |
| 2012/0143326 A1 | 6/2012 | Canovas et al. |
| 2012/0154740 A1 | 6/2012 | Bradley et al. |
| 2012/0170121 A1 | 7/2012 | Okada et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0107202 A1 | 5/2013 | Liang |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal et al. |
| 2016/0216535 A1 | 7/2016 | Zhao |
| 2016/0220350 A1 | 8/2016 | Gerlach |
| 2016/0220352 A1 | 8/2016 | Choi et al. |
| 2016/0320633 A1 | 11/2016 | Weeber et al. |
| 2016/0334640 A1 | 11/2016 | De, Jr. et al. |
| 2016/0341978 A1 | 11/2016 | Schwiegerling |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas Vidal et al. |
| 2017/0245986 A1 | 8/2017 | Canovas Vidal et al. |
| 2017/0245987 A1 | 8/2017 | Canovas Vidal et al. |
| 2017/0252151 A1 | 9/2017 | Mackool |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1* | 5/2018 | Hong .................. G02C 7/044 |
| 2018/0275428 A1* | 9/2018 | Ando .................. G02C 7/044 |
| 2018/0368972 A1 | 12/2018 | Rosen et al. |
| 2018/0373060 A1 | 12/2018 | Knox et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2020/0038172 A1 | 2/2020 | Hussain et al. |
| 2021/0196452 A1 | 7/2021 | Gounou et al. |

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 104918580 A | 9/2015 |
| CN | 108646434 A | 10/2018 |
| EP | 335731 A2 | 10/1989 |
| EP | 342895 A2 | 11/1989 |
| EP | 0369561 A2 | 5/1990 |
| EP | 375291 A2 | 6/1990 |
| EP | 412751 A2 | 2/1991 |
| EP | 0457553 A2 | 11/1991 |
| EP | 470811 A2 | 2/1992 |
| EP | 605841 A1 | 7/1994 |
| EP | 0316162 B1 | 10/1995 |
| EP | 355230 B1 | 10/1995 |
| EP | 681198 A1 | 11/1995 |
| EP | 0537643 B1 | 3/1997 |
| EP | 949529 A2 | 10/1999 |
| EP | 1376203 A2 | 1/2004 |
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2812882 A1 | 12/2014 |
| EP | 2813881 A1 | 12/2014 |
| EP | 2349093 B1 | 10/2015 |
| EP | 3179293 A1 | 6/2017 |
| EP | 3150170 B1 | 12/2017 |
| EP | 3415980 A1 | 12/2018 |
| EP | 2527908 B1 | 3/2019 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2013101323 A | 5/2013 |
| KR | 101154066 B1 | 6/2012 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | WO-9744689 A1 * | 11/1997 ........... A61F 2/1618 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |

(56) References Cited

FOREIGN PATENT DOCUMENTS

| WO | 2004090611 A2 | 10/2004 |
| --- | --- | --- |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013118177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2018093873 A1 | 5/2018 |
| WO | 2018150236 A1 | 8/2018 |
| WO | 2019002384 A1 | 1/2019 |
| WO | 2019130030 A1 | 7/2019 |
| WO | 2020115104 A1 | 6/2020 |

OTHER PUBLICATIONS

Morlock, R., et al., "Patient-Reported Spectacle Independence Questionnaire (PRSIQ): Development and Validation,"American Journal of Ophthalmology, Jun. 2017, vol. 178, pp. 101-114.
Albert D.M., "(Book Review) Intraocular Lenses: Evolution, Designs, Complications, and Pathology, by David Apple et al.," Archieves of Opthalmology, 1990, vol. 108, pp. 650.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alvarez S. L. et al., "Spectral threshold: measurement and clinical applications," British Journal of Ophthalmology, 1983, 67, 504-507.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Artal P., et al., "Contributions of the Cornea and the Lens to the Aberrations of the Human Eye," Optics Letters, 1998, vol. 23 (21), pp. 1713-1715.
Atchinson D.A., "Design of Aspheric Intraocular Lens," Ophthamic & Physiological Optics, 1991, vol. 11 (2), pp. 137-146.
Atchinson D.A., et al., "Optical Design of Intraocular Lenses. II. Off-Axis performance," Optometry & Vision Science, 1989, vol. 66 (9), pp. 579-590.
Atchinson D.A., et al., "Third-Order Aberrations Of Pseudophakic Eyes," Ophthalmic and Physiological Optics , 1989, vol. 9, pp. 205-211.
Atchinson D.A., "Optical Design of Intraocular Lenses. I. On-Axis Performance," American Academy of Optometry, 1989, vol. 66 (8), pp. 492-506.
Atchinson D.A., "Optical design of intraocular lenses III. On-Axis Performance in the Presence of Lens Displacement," American Academy of Optometry, 1989, vol. 66 (10), pp. 671-681.
Atchinson, "Refractive errors induced by displacement of intraocular lenses within the pseudophakic eye," Optometry & Vision Science, 1989, 66 (3), 146-152.
Bonnet R., et al., "New Method Of Topographical Ophthalmometry—Its Theoretical And Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al., "Optical Performance Of Holographic Kinoforms," Applied Optics, Mar. 1989, vol. 28 (5), pp. 976-983.
Canovas C., et al., "Hybrid Adaptive-Optics Visual Simulator," Optical Letters, Jan. 15, 2010, vol. 35 (2), pp. 196-198.
Castignoles F., et al., "Comparison of the Efficiency, MTF and Chromatic Properties of Four Diffractive Bifocal Intraocular Lens Designs, " Optics Express, Mar. 2010, vol. 18 (5), pp. 5245-5256.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Dwyer W. O. et al., "Racial Differences In Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
Futhey J.A., "Diffractive Bifocal Intraocular Lens," SPIE, 1989, vol. 1052, pp. 142-148.
Geun Y., et al., "Visual Performance after Correcting the Monchromatic and Chromatic Aberrations of the Eye," Journal of the Optical Society of America, 2002, vol. 19 (2), pp. 266-275.
Glasser A. et al., "Presbyopia and the optical changes in the human crystalline lens with age," Vision Res, 1998, 38 (2), 209-229.
Greivenkamp J.E., et al., "Visual Acuity Modeling Using Optical Raytracing Of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.
Guirao A., et al., "Corneal Wave Aberration from Videokeratography: Accuracy And Limitations of the Procedure," Journal of the Optical Society of America, 2000, vol. 17 (6), pp. 955-965.

(56) References Cited

OTHER PUBLICATIONS

IOVS, 1999, 40 (4), S535.

Kiely et al., "The mean shape of the human cornea," Optica ACTA, 1982, 29 (8), 1027-1040.

Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.

Liang J., et al, "Objective Measurement Of Wave Aberrations Of The Human Eye With The Use Of A Hartmann-Shack Wave-Front Sensor," Journal of the Optical Society of America, 1994, vol. 11 (7), pp. 1949-1957.

Lindsay R., et al., "Descriptors of Corneal Shape," Optometry and Vision Science, 1998, vol. 75 (2), pp. 156-158.

Liou H.L., et al., "Anatomically Accurate, Finite Model Eye for Optical Modeling," Journal of Optical Society of America, Aug. 1997, vol. 14 (8), pp. 1684-1695.

Lotmar, "Theoretical eye model with aspherics," Journal of the Optical Society of America, 1971, 61 (11), 1522-1529.

Malacara D., et al., "Wavefront Fitting With Discrete Orthogonal Polynomials In a Unit Radius Circle," Optical Engineering, 1990, vol. 29 (6), pp. 672-675.

Mandell R.B., et al., "Mathematical Model of the Corneal Contour," 1965, School of Optometry, University of California, Berkeley, pp. 183-197.

Marcos S., et al., "A New Approach to the Study of Ocular Chromatic Aberrations," Vision Research, 1999, vol. 39 (26), pp. 4309-4323.

Marsack J.D., et al., "Metrics of Optical Quality Derived from Wave Aberrations Predict Visual Performance," Journal of Vision, Apr. 2004, vol. 4 (4), pp. 322-328.

Monsoriu J.A., et al., "Devil's Lenses," Optics Express, Oct. 17, 2007, vol. 15 (21), pp. 13858-13864.

Mordi J.A., et al., "Influence of Age of Chromatic Aberration of the Human Eye," American Journal of Optometry & Physiological Optics, 1985, vol. 62 (12), pp. 864-869.

Navarro R., et al., "Accommodation-Dependent Model of the Human Eye with Aspherics," Journal of the Optical Society of America, Aug. 1985, vol. 2 (8), pp. 1273-1281.

Norrby S., et al., "Model Eyes for Evaluation of Intraocular Lenses," Applied Optics, Sep. 7, 2007, vol. 46 (26), pp. 6595-6605.

"Optical Design," Military Standardization Handbook, 1962, Chapter 4, U.S. Department of Defense MIL-HDBK-141, 4-1-4-19.

Oshika T., et al., "Changes in Corneal Wavefront Aberrations with Aging," Investigative Ophthalmology & Visual Science, 1999, vol. 40 (7), pp. 1351-1355.

Patel S., et al., "Shape and Radius of Posterior Corneal Surface," Refractive and Corneal Surgery, 1993, vol. 9 (3), pp. 173-181.

Piers P.A., et al., "Eye Models for the Prediction of Contrast Vision in Patients with New Intraocular Lens Designs," Optics Letters, Apr. 1, 2004, vol. 29 (7), pp. 733-735.

PIERS P.A., et al., "Theoretical Comparison of Aberration-Correcting Customized and Aspheric Intraocular Lenses," Journal of Refractive Surgery, Apr. 2007, vol. 23 (4), pp. 374-384.

Said et al., "The Variation with Age of the Spectral Transmissivity of the Living Human Crystalline Lens," Gerontologia, 1959, 213-231.

Schwiegerling et al., "Representation of videokeratoscopic height data with Zernike polynomials," Journal of the Optical Society of America, 1995, 12 (10), 2105-2113.

Seitz B., et al., "Corneal Topography," Current Opinion in Ophthalmolgy, 1997, vol. 8 (4), pp. 8-24.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Smith G., et al., "The Spherical Aberration of the Crystalline Lens of the Human Eye," Vision Res., 2001, vol. 41 (2), pp. 235-243.

Smith Kinney, "Sensitivity of the eye to spectral radiation at scotopic and mesopic intensity levels," Journal of the Optical Society of America, 1955, 45 (7), 507-514.

Sokołowski M., et al. "Hybrid Heptafocal Intraocular Lenses," Optica Applicata, Dec. 2015, vol. 45 (3), pp. 285-298.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Thibos L. N. et al., "The chromatic eye: a new reduced-eye model of ocular chromatic aberration in humans," Applied Optics, 1992, 31 (19), 3594-3600.

Thibos L. N. et al., "Theork and measurement of ocular chromatic aberration," Vision Res, 1988, 30 (1), 33-49.

Townsley, "New Knowledge of the corneal contour," Contacto, 1970, pp. 38-43.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Verriest G., "The Spectral Curve of Relative Luminous Efficiency in Different Age Groups of Aphakic Eyes," Mod Probl Ophthalmol., 1974, 13, 314-317.

Villegas E.A., et al., "Correlation between Optical and Psychophy, Sical Parameters as a Function of Defocus," Optometry and Vision Science, Jan. 1, 2002, vol. 79 (1), pp. 60-67.

Wang J.Y., et al, "Wave-Front Interpretation With Zernike Polynomials," Applied Optics, 1980, vol. 19 (9), pp. 1510-1518.

* cited by examiner

DIFFRACTIVE LENSES FOR PRESBYOPIA TREATMENT

CROSS REFERENCE TO RELATED APPLICATIONS

This application is a U.S. national stage of and claims the benefit under 35 U.S.C. § 371 of International Patent Application No. PCT/EP2019/083615, filed Dec. 4, 2019, which claims priority to, and the benefit of, under 35 U.S.C. § 119 (e) of U.S. Provisional Appl. No. 62/776,362, filed Dec. 6, 2018, all of which are incorporated by reference herein in their entirety.

BACKGROUND

Embodiments of the present invention relate to vision treatment techniques and in particular, to ophthalmic lenses such as, for example, contact lenses, corneal inlays or onlays, or intraocular lenses (IOLs) including, for example, phakic IOLs and piggyback IOLs (ie. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. At the very least, since a monofocal IOL provides vision treatment at only one distance and since the typical correction is for far distance, spectacles are usually needed for good vision at near distances and sometimes for good vision at intermediate distances. The term "near vision" generally corresponds to vision provided when objects are at a distance from the subject eye at equal; or less than 1.5 feet. The term "distant vision" generally corresponds to vision provided when objects are at a distance of at least about 5-6 feet or greater. The term "intermediate vision" corresponds to vision provided when objects are at a distance of about 1.5 feet to about 5-6 feet from the subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near (add) power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. While multifocal ophthalmic lenses typically provide adequate near and far vision, intermediate vision may be compromised.

A lens with an extended range of vision may thus provide certain patients the benefits of good vision at a range of distances, while having reduced or no dysphotopsia. Various techniques for extending the depth of focus of an IOL have been proposed. One technique is embodied in the Tecnis Symfony® lens offered by Johnson & Johnson Vision. One technique may include a bulls-eye refractive principle, and may involve a central zone with a slightly increased power. One technique may include an asphere or include refractive zones with different refractive zonal powers.

Although certain proposed treatments may provide some benefit to patients in need thereof, further advances would be desirable. For example, it would be desirable to provide improved IOL systems and methods that confer enhanced image quality across a wide and extended range of foci without dysphotopsia. Embodiments of the present invention provide solutions that address the problems described above, and hence provide answers to at least some of these outstanding needs.

BRIEF SUMMARY

Embodiments herein described include ophthalmic lenses including an optic including a first surface and a second surface each disposed about an optical axis and extending radially outward from the optical axis to an outer periphery of the optic, the first surface facing opposite the second surface. A diffractive profile including a plurality of echelettes may be disposed on the first surface such that no echelette on the first surface repeats between the optical axis and the outer periphery of the optic.

Embodiments herein described include ophthalmic lenses including an optic including a first surface and a second surface each disposed about an optical axis and extending radially outward from the optical axis to an outer periphery of the optic, the first surface facing opposite the second surface. A diffractive profile including a plurality of echelettes may be disposed on the first surface such that each echelette on the first surface between the optical axis and the outer periphery of the optic has a profile in r-squared space that is different than a profile in r-squared space of any other echelette on the first surface between the optical axis and the outer periphery of the optic.

Embodiments herein described include ophthalmic lenses with a first surface and a second surface disposed about an optical axis and facing opposite each other. A diffractive profile may be disposed on the first surface and may include a plurality of echelettes. At least one of the plurality of echelettes may be connected to an adjacent echelette by a step height of zero.

Embodiments herein described include ophthalmic lenses including an optic including a first surface and a second surface each disposed about an optical axis and extending radially outward from the optical axis to an outer periphery of the optic, the first surface facing opposite the second surface and including a radially extending zone positioned between the optical axis and the outer periphery of the optic. A diffractive profile including a plurality of echelettes may be disposed on the first surface within the radially extending zone such that no echelette repeats within the radially extending zone.

Embodiments herein described also include manufacturing systems for making an ophthalmic lens. Such manufacturing systems can include an input that accepts an ophthalmic lens prescription for a patient eye. A first module is configured to generate a diffractive profile based on the ophthalmic lens prescription. The diffractive profile may include a plurality of echelettes and the diffractive profile disposed on an optical surface of an optic such that no echelette on the optical surface repeats between an optical axis and an outer periphery of the optic. The manufacturing system may include a manufacturing assembly that fabricates the ophthalmic lens based on the diffractive profile.

Embodiments herein described also include manufacturing systems for making an ophthalmic lens. Such manufacturing system can include an input that accepts an ophthalmic lens prescription for a patient eye. A first module is configured to generate a diffractive profile based on the ophthalmic lens prescription. The diffractive profile may include a plurality of echelettes for being disposed on an optical surface of an optic, and at least one of the plurality of echelettes may be connected to an adjacent echelette by a step height of zero. The manufacturing system may include a manufacturing assembly that fabricates the ophthalmic lens based on the diffractive profile.

Embodiments herein described also include methods of designing an intraocular lens. Such methods can include defining a diffractive profile and generating a diffractive lens surface based on the diffractive profile. The diffractive profile may include a plurality of echelettes and the diffractive profile disposed on an optical surface of an optic such that no echelette on the optical surface repeats between an optical axis and an outer periphery of the optic.

Embodiments herein described also include methods of designing an intraocular lens. Such methods can include defining a diffractive profile and generating a diffractive lens surface based on the diffractive profile. The diffractive profile may include a plurality of echelettes disposed on an optical surface of an optic, and at least one of the plurality of echelettes may be connected to an adjacent echelette by a step height of zero.

DETAILED DESCRIPTION

Contemporary Lens Shapes and Diffractive Profiles

FIGS. 1A, 1B, 2A, 2B, 3A and 3B illustrate multifocal IOL lens geometries, aspects of which are described in U.S. Patent Publication No. 2011-0149236 A1, which is hereby incorporated by reference in its entirety.

Figure 1A:
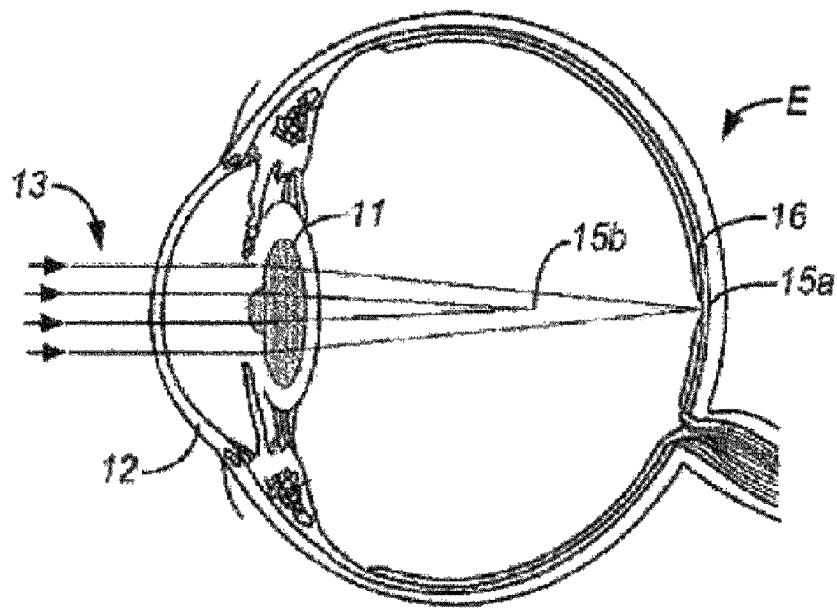
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
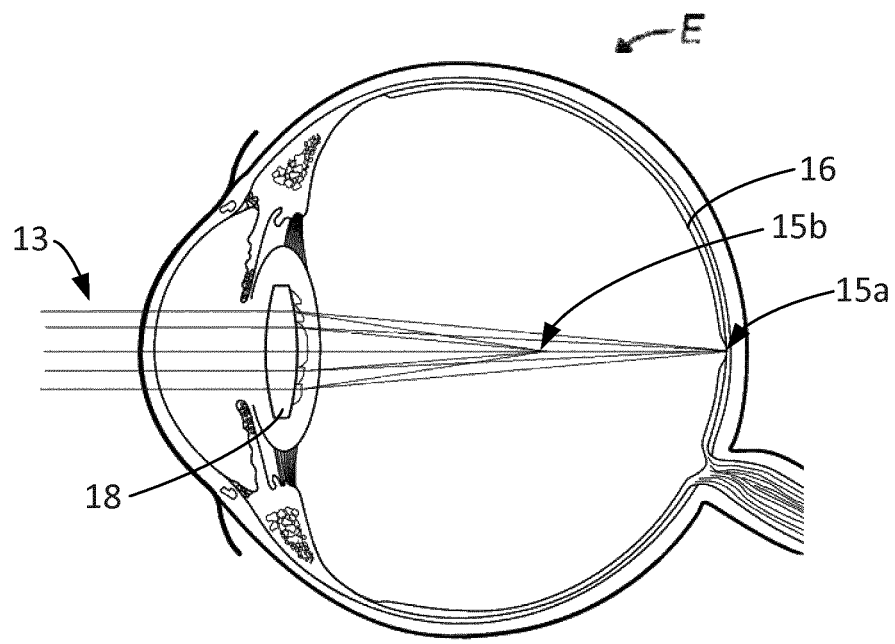
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be disposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15$a$ on retina 16 for viewing distant objects and a near field focus 15$b$ for viewing objects close to the eye. Depending on the distance from the source of light 13, the focus on retina 16 may be the near field focus 15$b$ instead. Typically, far field focus 15$a$ is associated with $0^{th}$ diffractive order and near field focus 15$b$ is associated with the $1^{st}$ diffractive order, although other orders may be used as well.

Bifocal ophthalmic lens 18 typically distributes the majority of light energy into two viewing orders, often with the goal of splitting imaging light energy about evenly (50%: 50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
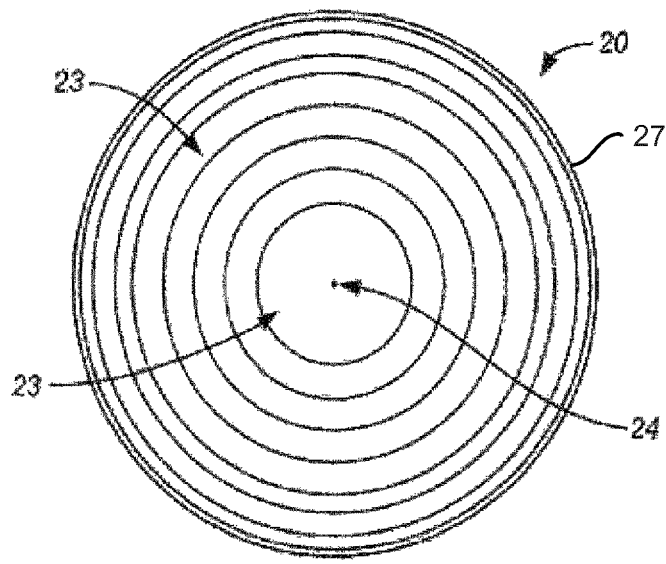
FIG. 2A illustrates a front view of a diffractive multifocal intraocular lens.
Figure 2B:
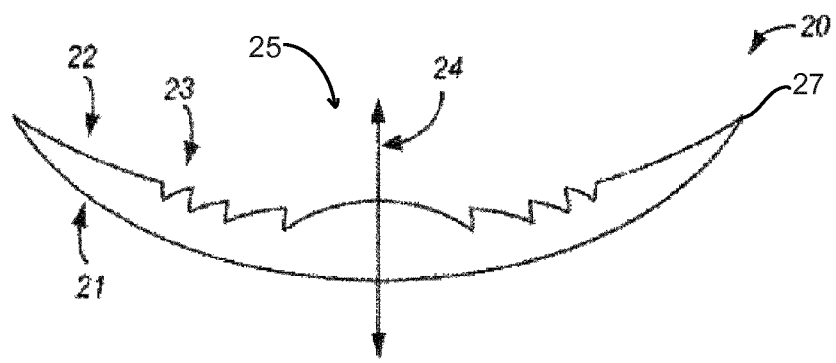
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about optical axis 24. The faces 21, 22, or optical surfaces, extend radially outward from the optical axis 24 to an outer periphery 27 of the optic. The faces 21, 22, or optical surfaces, face opposite each other.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be disposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
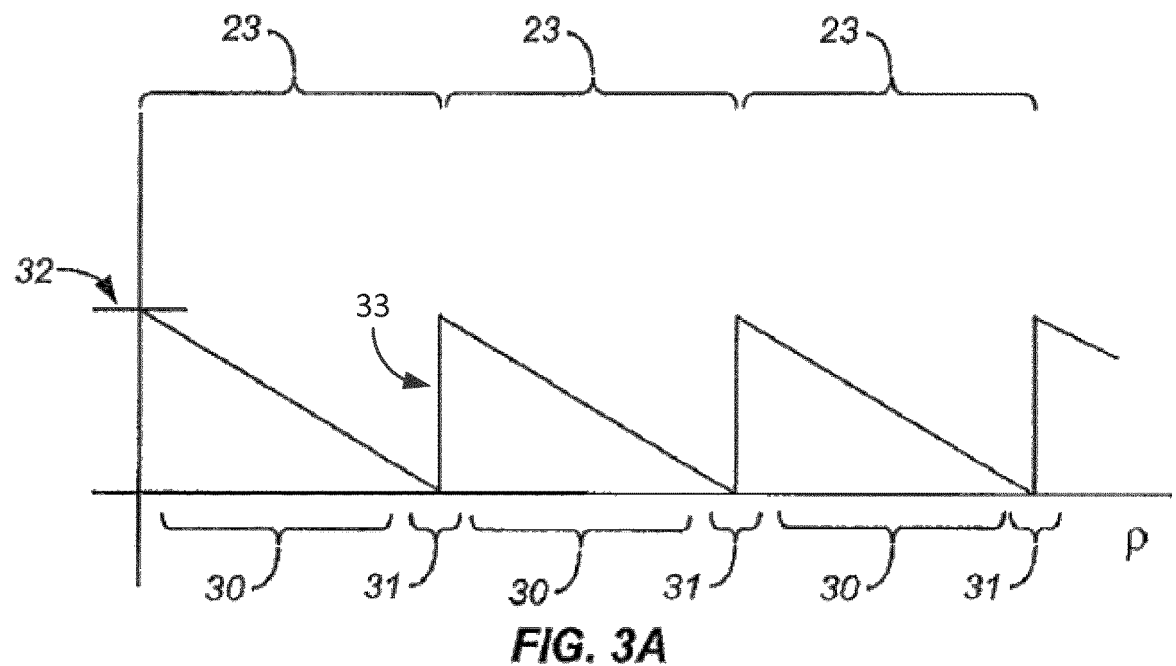
FIGS. 3A-3B are graphical representations of a portion of the diffractive profile of a conventional diffractive multifocal lens.
Figure 3B:
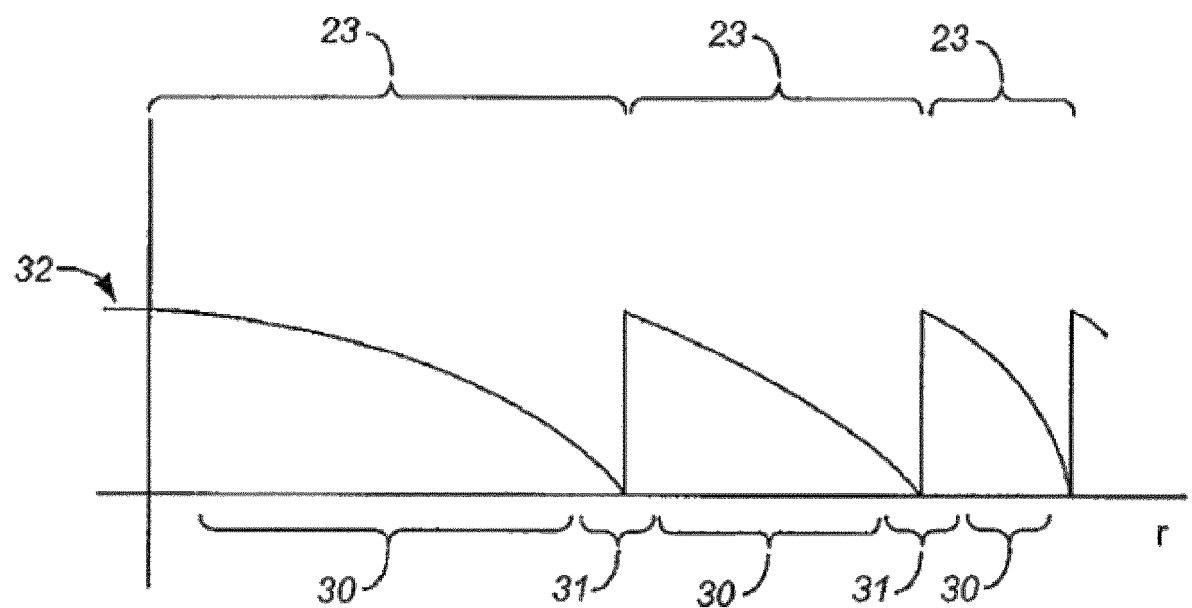

FIGS. 3A and 3B are graphical representations of a portion of a typical diffractive profile of a multifocal lens. While the graph shows only 3 echelettes, typical diffractive lenses extend to at least 9 echelettes to over 32 echelettes. In FIG. 3A, the height 32 of the surface relief profile (from a plane perpendicular to the light rays) of each point on the echelette surface is plotted against the square of the radial distance ($r^2$ or $\rho$) from the optical axis of the lens (referred to as r-squared space). In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that is parabolic as shown in FIG. 3B. The slope of each echelette in r-squared space (shown in FIG. 3A), however, is the same. As for the typical diffractive multifocal lens, as shown here, all echelettes have the same surface area. The area of echelettes 23 determines the diffractive power of lens 20, and, as area and radii are correlated, the diffractive power is also related to the radii of the echelettes. The physical offset of the trailing edge of each echelette to the leading edge of the adjacent echelette is the step height. An exemplary step height between adjacent echelettes is marked as reference number 33 in FIG. 3A. The step heights remain the same in r-squared space (FIG. 3A) and in linear space (FIG. 3B). The step offset is the height offset of the transition zone from the underlying base curve. An exemplary step offset is marked as reference number 412 in FIG. 4.

Conventional multifocal diffractive lenses typically provide for near and far vision, neglecting visual performance at intermediate distances. Providing for an extended range of vision can help to improve the visual performance at intermediate distances. In addition, providing for a zero-step height between transition zones may reduce visual artifacts such as halos or glare that may otherwise be visible to a user due to one or more of the boundaries between the optical zones.

Figure 4:
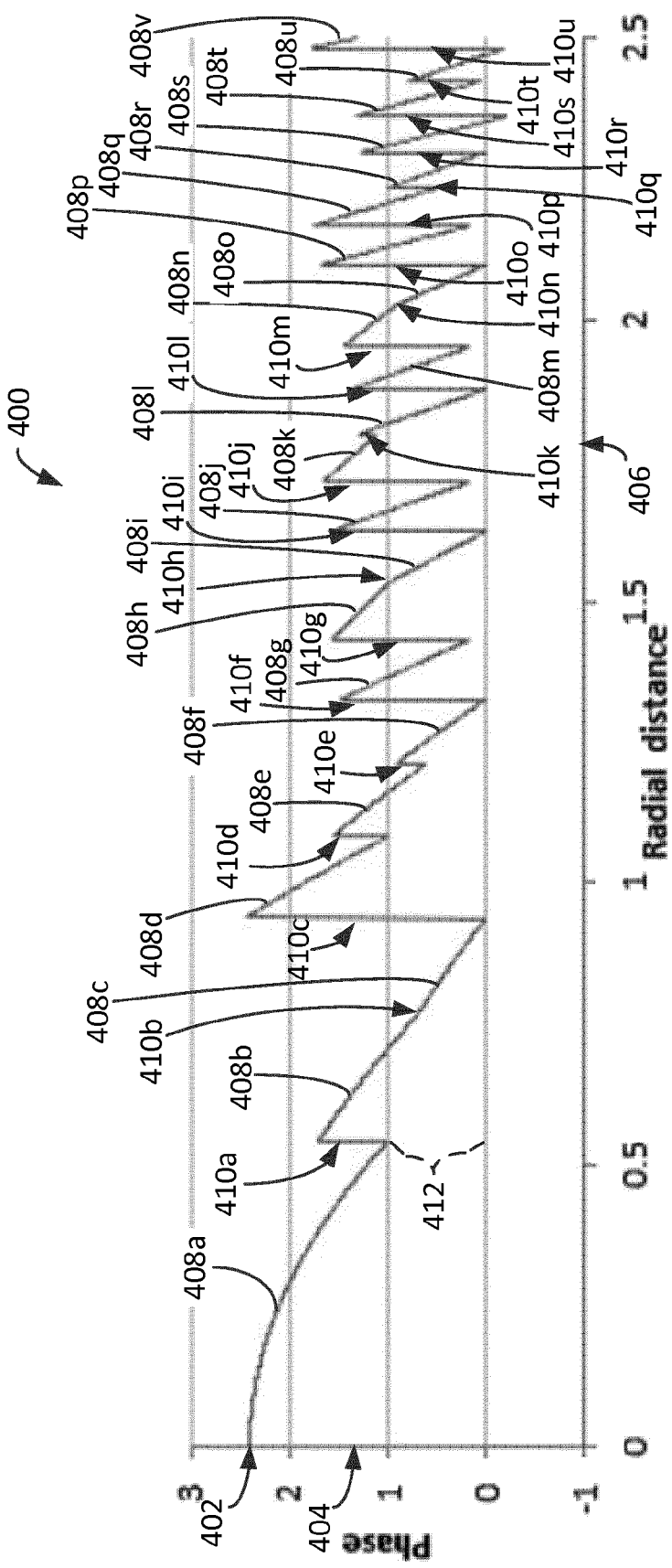
FIG. 4 is a graphical representation illustrating a lens profile for a diffractive lens according to certain embodiments of this disclosure.

FIG. 4 shows a graphical representation illustrating an embodiment of a diffractive profile 400. The diffractive profile 400 may result in a lens having an extended range of vision or a lens that provides good vision over the entire range from far to near distances.

The diffractive profile 400, in the form of a sag profile, is shown extending outward from an optical axis 402. The diffractive zones, or echelettes, are shown extending radially outward from the optical axis 402, and would be arranged around the optical axis 402 (the other half of the diffractive profile 400 is not shown). The diffractive profile 400 is shown relative to the Y axis 404, which represents the phase shift of the diffractive profile 400. The height is shown in units of wavelengths, and may represent the distance from the base spherical wavefront generated by the lens. In other embodiments, other units or scalings may be utilized. The diffractive profiles disclosed herein may be disposed on optics such as the optics described in regard to FIGS. 2A and 2B, among other types of optics.

The height or phase shift of the diffractive profile 400 is shown in relation to the radius on the X axis 406 from the optical axis 402. The radial coordinate represents the distance from the optical axis 402, and is shown in units of millimeters, although in other embodiments, other units or scalings may be utilized. The diffractive profile 400 may extend outward from the optical axis 402 for a radius of 2.5 millimeters (diameter of 5.0 millimeters), although in other embodiments the diffractive profile 400 may extend for a lesser or greater radius.

The diffractive profile 400 includes a plurality of diffractive zones or echelettes. The diffractive profile 400 may be disposed on an optical surface of the optic between the optical axis 402 and the outer periphery of the optic. The plurality of echelettes 408a-v are positioned on the surface of the optic between the optical axis 402 and the outer periphery of the optic.

The diffractive profile 400 may include twenty-two echelettes 408a-v. The first echelette 408a is adjacent the optical axis 402. The echelettes 408a-v are connected by respective transition zones 410a-u.

Each echelette 408a-v has a profile defined by the shape or slope of the respective echelette 408a-v. Each echelette 408a-v as shown in FIG. 4 has the same area as each other echelette 408a-v. Each echelette 408a-v has a different slope than each other in r-squared space and has a different profile from each other in r-squared space.

The diffractive profile 400 is disposed on the optical surface such that no echelette 408a v on the optical surface repeats between the optical axis 402 and the outer periphery of the optic. As shown in FIG. 4, each echelette 408a-v does not repeat on the surface of the optic between the optical axis 402 and the outer periphery of the optic. Each echelette 408a-v that is on the optical surface between the optical axis 402 and the outer periphery of the optic has a profile in r-squared space that is different than a profile in r-squared space of any other echelette 408a-v that is on the optical surface between the optical axis 402 and the outer periphery of the optic. As shown in FIG. 4, none of the echelettes that are present on the optic are repeated over the entirety of the optical surface of the optic.

As shown in FIG. 4, the diffractive profile 400 may extend over the entirety of the radial extent of the optic from the optical axis 402 to the outer periphery of the optic. In one embodiment, a diffractive profile may extend over only a portion of the radial extent of the optic from the optical axis to the outer periphery of the optic, yet still be configured such that no echelette on the optical surface repeats between the optical axis 402 and the outer periphery of the optic. For example, the diffractive profile may not fill the entirety of the radial extent of the optic from the optical axis to the outer periphery of the optic (such as only filling one millimeter of two millimeters of the radial extent), yet that diffractive profile (between the optical axis of the outer periphery of the optic) may still be configured such that no echelette on the optical surface repeats between the optical axis 402 and the outer periphery of the optic. For example, only two or five echelettes may be present on the entirety of the optical surface, yet each may have a different profile than each other (in real space and in r-squared space).

The step heights of the echelettes 408a-v increase as the echelettes 408a-v are positioned radially outward from the optical axis 402 and decrease as the echelettes 408a-v are positioned radially outward from the optical axis 402. The diffractive profile 400 may include a combination of increasing step heights and decreasing step heights (or greater or lesser step heights). For example, a first echelette positioned radially outward of a second echelette may have a greater step height than the second echelette. A third echelette may be positioned radially outward of the second echelette may have a lesser step height than the second echelette. A varied combination of greater and lesser step heights may be utilized as desired. The step offsets of the echelettes 408a v increase as the echelettes 408a-v are positioned radially outward from the optical axis 402 and decrease as the echelettes 408a-v are positioned radially outward from the optical axis 402. The diffractive profile 400 may include a combination of increasing step offsets and decreasing step offsets (or greater or lesser step offsets). For example, a first echelette positioned radially outward of a second echelette may have a greater step offset than the second echelette. A third echelette may be positioned radially outward of the second echelette may have a lesser step offset than the second echelette. The diffractive profile 400 may include a combination of both increasing and decreasing step heights and step offsets for the echelettes 408a-v. The combinations may be as shown in FIG. 4 (or in Table 1 below) or in other embodiments a greater or lesser number of increasing and decreasing step heights and step offsets for the echelettes may be utilized.

The radius of the optic may be varied in embodiments. As shown in FIG. 4, the radius from the optical axis 402 to the outer periphery of the optic may be 2.5 millimeters. In other embodiments, other radiuses may be utilized. For example, a radius may be 4 millimeters in one embodiment. In one embodiment, the radius may be between 2 and 4 millimeters. The radius of the diffractive profile 400 may fill the radius of the optic or may be a lesser radius (for example the diffractive profile radius being less than 2.5 millimeters for an optic having a radius of 2.5 millimeters). Thus, the diffractive profile may extend outward from the optical axis 402 to a lesser radius (and diameter) than the radius (and diameter) of the optic.

A diffractive profile according to embodiments herein may include a variety of numbers of echelettes. For example, in one embodiment the diffractive profile may include at least two echelettes. In one embodiment, the diffractive profile may include at least five echelettes. In one embodiment, the diffractive profile may include at least twelve echelettes. In one embodiment, the diffractive profile may include at least thirty echelettes. In one embodiment, the diffractive profile may include at least thirty-two echelettes. In one embodiment, at least 60 echelettes may be utilized. In one embodiment, between 30 and 64 echelettes may be utilized, inclusive. Other numbers of echelettes may be utilized and may be utilized, which may be according to the size of the optic to be used. The echelettes may each be configured to not repeat on the optical surface, as represented in FIG. 4.

In one embodiment, at least one of the plurality of echelettes 408a-v may be connected to an adjacent echelette by a step height of zero. For example, transition zones 410b, 410h, 410n each have a step height of zero between the respective adjacent echelettes (408b, 408c, 408h, 408i, 408n, 408o). The step height of zero may reduce visual artifacts such as halos or glare that may otherwise be visible to a user due to one or more of the boundaries between the optical zones.

In embodiments, the number of transitions having a step height of zero may be varied from that shown in FIG. 4. For example, in one embodiment, only one transition may have a step height of zero (such that one echelette is connected to an adjacent echelette by a step height of zero). In one embodiment, two transitions may have a step height of zero (such that two echelettes are connected to an adjacent echelette by a step height of zero). In one embodiment, three transitions may have a step height of zero (such that three echelettes are connected to an adjacent echelette by a step height of zero, and accordingly six total echelettes are connected to an adjacent echelette by a step height of zero counting the adjacent echelettes). In other embodiments, a greater or lesser number of transitions having a step height of zero may be utilized. For example, at least one of the plurality of echelettes may have a step height of zero. In one embodiment, at least three of the plurality of echelettes may have a step height of zero. In one embodiment, at least six of the plurality of echelettes may have a step height of zero. The step heights of zero may be positioned between echelettes in a variety of locations as desired.

The transitions having a step height of zero may be implemented in combination with, or separate from the diffractive profile 400 disposed on the optical surface such that no echelette on the optical surface repeats between the optical axis 402 and the outer periphery of the optic. The echelettes 408a-v each not repeating on the surface of the optic between the optical axis 402 and the outer periphery of the optic may serve to distribute light over a range from a far focal length to a near focal length, and may enhance the depth of focus for the user.

Table 1 below illustrates an exemplary step height and step offset of a diffractive profile according to an embodiment of the present disclosure. The step heights and step offsets of the echelettes of the diffractive profile are provided in units of micrometers. As shown, the step heights and step offsets of each echelette of the diffractive profile are different from each other. The echelettes have a different profile than each other (in real space and in r-squared space). Certain echelettes have a step height of zero (at transition zones 2, 8, 14, 20, and 23).

TABLE 1

| Transition Zone | Step Height | Step Offset |
|---|---|---|
| 0 | 9.851 | 0.000 |
| 1 | 2.873 | 4.104 |
| 2 | 0.000 | 2.873 |
| 3 | 10.028 | 0.000 |
| 4 | 2.317 | 4.098 |
| 5 | 1.261 | 2.523 |
| 6 | 6.034 | 0.000 |
| 7 | 5.746 | 0.616 |
| 8 | 0.000 | 4.104 |
| 9 | 6.444 | 0.000 |
| 10 | 6.157 | 0.616 |
| 11 | 0.821 | 4.515 |
| 12 | 5.623 | 0.000 |
| 13 | 5.336 | 0.616 |
| 14 | 0.000 | 3.694 |
| 15 | 6.854 | 0.000 |
| 16 | 6.567 | 0.698 |
| 17 | 2.052 | 2.052 |
| 18 | 5.213 | 0.000 |
| 19 | 4.925 | 0.534 |
| 20 | 0.000 | 3.284 |
| 21 | 7.265 | 0.000 |
| 22 | 6.978 | 0.739 |
| 23 | 0.000 | 5.336 |

The diffractive profile 400 and the diffractive profile represented in Table 1 above may be utilized to provide a good visual quality distributed within a range from far to near, and may reduce photic phenomena and scatter. The diffractive profiles may be utilized to enhance the contrast sensitivity of the lens.

The diffractive profile 400 and the diffractive profile represented in Table 1 may be utilized to reduce chromatic aberration in the far focus. The diffractive profile 400 and the diffractive profile represented in Table 1 may be utilized to reduce chromatic aberration of the lens or the eye by adding a diffractive power to contribute to the far focus of the lens.

Figure 5:
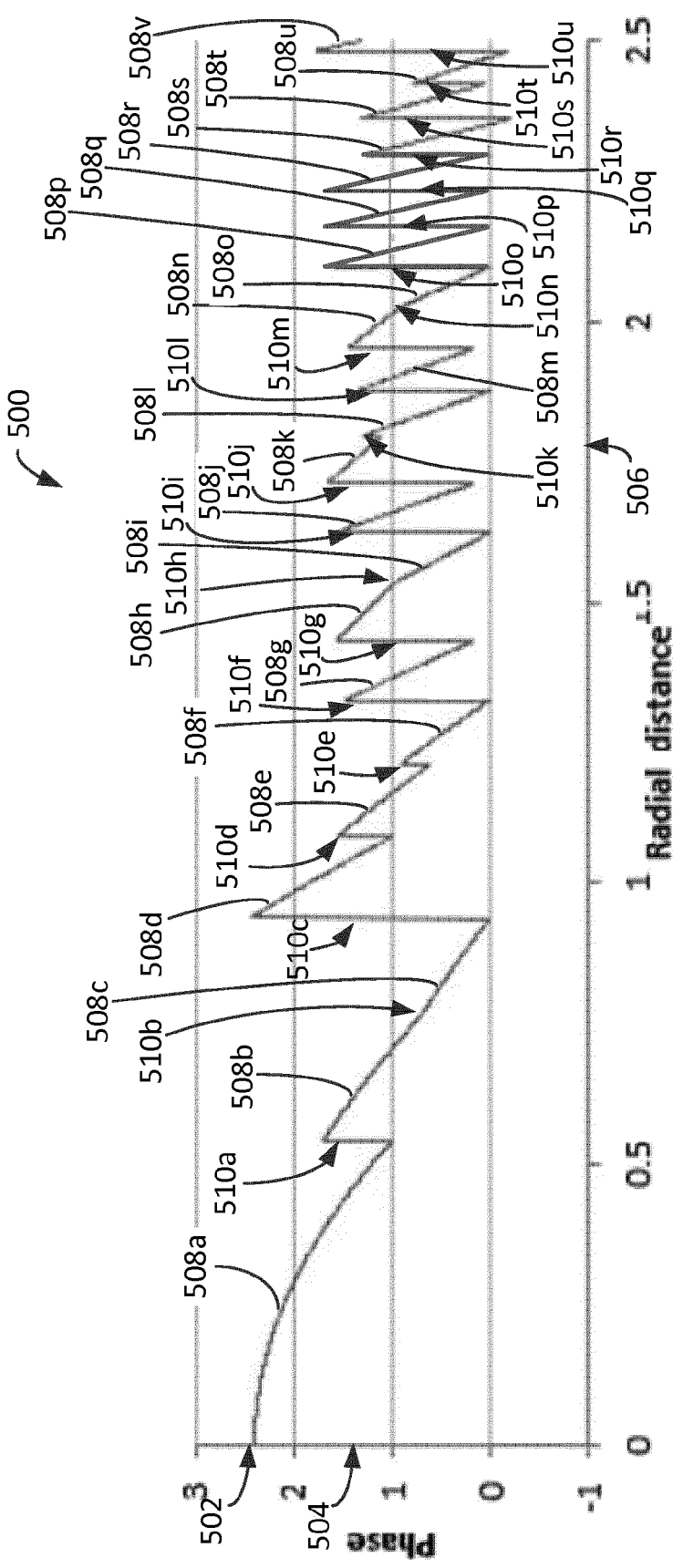
FIG. 5 is a graphical representation illustrating a lens profile for a diffractive lens according to certain embodiments of this disclosure.

In one embodiment, only a portion of the optical surface between the optical axis and the outer periphery of the optic may include echelettes that do not repeat on the optical surface. For example, in one embodiment, an optical surface may include a radially extending zone positioned between the optical axis and the outer periphery of the optic. A diffractive profile may include a plurality of echelettes and be disposed on the optical surface within the radially extending zone such that no echelette repeats within the radially extending zone. The optical surface may include another radially extending zone in which echelettes are repeated within the other radially extending zone. FIG. 5 illustrates such an embodiment. As such, in FIG. 5, the diffractive profile is configured such that at least one echelette on the optical surface repeats on the optical surface between the optical axis and the outer periphery of the optic.

FIG. 5 illustrates an embodiment in which the optic includes a diffractive profile 500 in which a portion of the optical surface includes echelettes that repeat on the optical surface. The diffractive profile 500, in the form of a sag profile, is shown extending outward from an optical axis 502. The diffractive zones, or echelettes, are shown extending radially outward from the optical axis 502, and would be arranged around the optical axis 502 (the other half of the diffractive profile 500 is not shown). The diffractive profile 500 is shown relative to the Y axis 504, which represents the phase shift of the diffractive profile 500. The height is shown in units of wavelengths, and may represent the distance from the base spherical wavefront generated by the lens. In other embodiments, other units or scalings may be utilized. The height or phase shift of the diffractive profile 500 is shown in relation to the radius on the X axis 506 from the optical axis 502. The radial coordinate represents the distance from the optical axis 502, and is shown in units of millimeters, although in other embodiments, other units or scalings may be utilized.

The diffractive profile 500 includes a plurality of echelettes 508a-v separated by transition zones 510a-u. The diffractive profile 500 includes a radially extending zone that extends from the optical axis 502 to the transition zone 510o. The radially extending zone may be considered a central zone, and includes echelettes 508a-o that each do not repeat within the radially extending central zone. The diffractive profile 500 however, includes another zone extending radially outward from the central zone, and starting with transition zone 510o. This zone may be considered a peripheral zone and includes echelettes 508p-r that do repeat within this radially extending peripheral zone. The echelettes 508p-r have the same profile as each other in r-squared space. As shown, three repeating echelettes 508p-r are shown, but in other embodiments a greater or lesser number may be utilized (e.g., at least one echelette that repeats within the zone). The number of echelettes within the zones may be varied as desired. In embodiments, sets of echelettes may be repeated within zones as desired. The locations of the zones may be varied as desired. For example, a radially extending zone may be merely positioned between the optical axis and the outer periphery of the optic. In one embodiment, a radially extending zone may be a central zone extending outward from the optical axis 502 as shown in FIG. 5. In one embodiment, a radially extending zone may be an intermediate zone between two zones. For example, the zone shown in FIG. 5 that starts with transition zone 510o may be considered an intermediate zone in view of the non-repeating echelette zone that starts at transition 510r and extends radially outward towards the outer periphery of the optic (and includes non-repeating echelettes 508s-v). The non-repeating echelette zone may thus be considered a peripheral zone adjacent the intermediate zone that has repeating echelettes. Any number of radially extending zones may be provided on the optical surface as desired.

The zones may either include non-repeating echelettes or repeating echelettes as desired. The zones may be sized and positioned as desired. For example, in one embodiment, a central radially extending zone may extend from the optical axis 502 for a radial distance of 1.5 millimeters. In one embodiment, a central radially extending zone may extend from the optical axis 502 for a radial distance of 2.5 millimeters. The radially extending zone may be configured such that no echelette within the radially extending zone is repeated within the radially extending zone. In one embodiment, such as the embodiment shown in FIG. 4, the radially extending zone may extend radially outward from the optical axis 402 to the outer periphery of the optic, and may only include echelettes that do not repeat within the radially extending zone. In other embodiments, other zones with repeating echelettes may be included as desired.

In one embodiment, an opposite optical surface of the optic may include repeating echelettes. For example, in the embodiment shown in FIG. 4, an opposite facing optical surface (such as surface 21 facing opposite surface 22) may include a diffractive profile having at least one echelette that repeats on the opposite optical surface.

The diffractive profiles disclosed herein may vary from the profiles 400, 500 shown in FIGS. 4 and 5. The number and configuration of echelettes 408, 508 and transition zones 410, 510 may also be varied as desired.

In one embodiment, the diffractive profiles 400, 500 may be positioned on a surface of a lens that is opposite an aspheric surface. The aspheric surface on the opposite side of the lens may be designed to reduce corneal spherical aberration of the patient.

In one embodiment, one or both surfaces of the lens may be aspherical, or include a refractive surface designed to extend the depth of focus, or create multifocality.

In one embodiment, a refractive zone on one or both surfaces of the lens may be utilized that may be the same size or different in size as one of the diffractive zones. The refractive zone includes a refractive surface designed to extend the depth of focus, or create multifocality.

Any of the embodiments of lens profiles discussed herein may be apodized to produce a desired result. The apodization may result in the step heights and step offsets of the echelettes being gradually varied according to the apodization, as to gradually increasing the amount of light in the distance focus as a function of pupil diameter.

Figure 6:
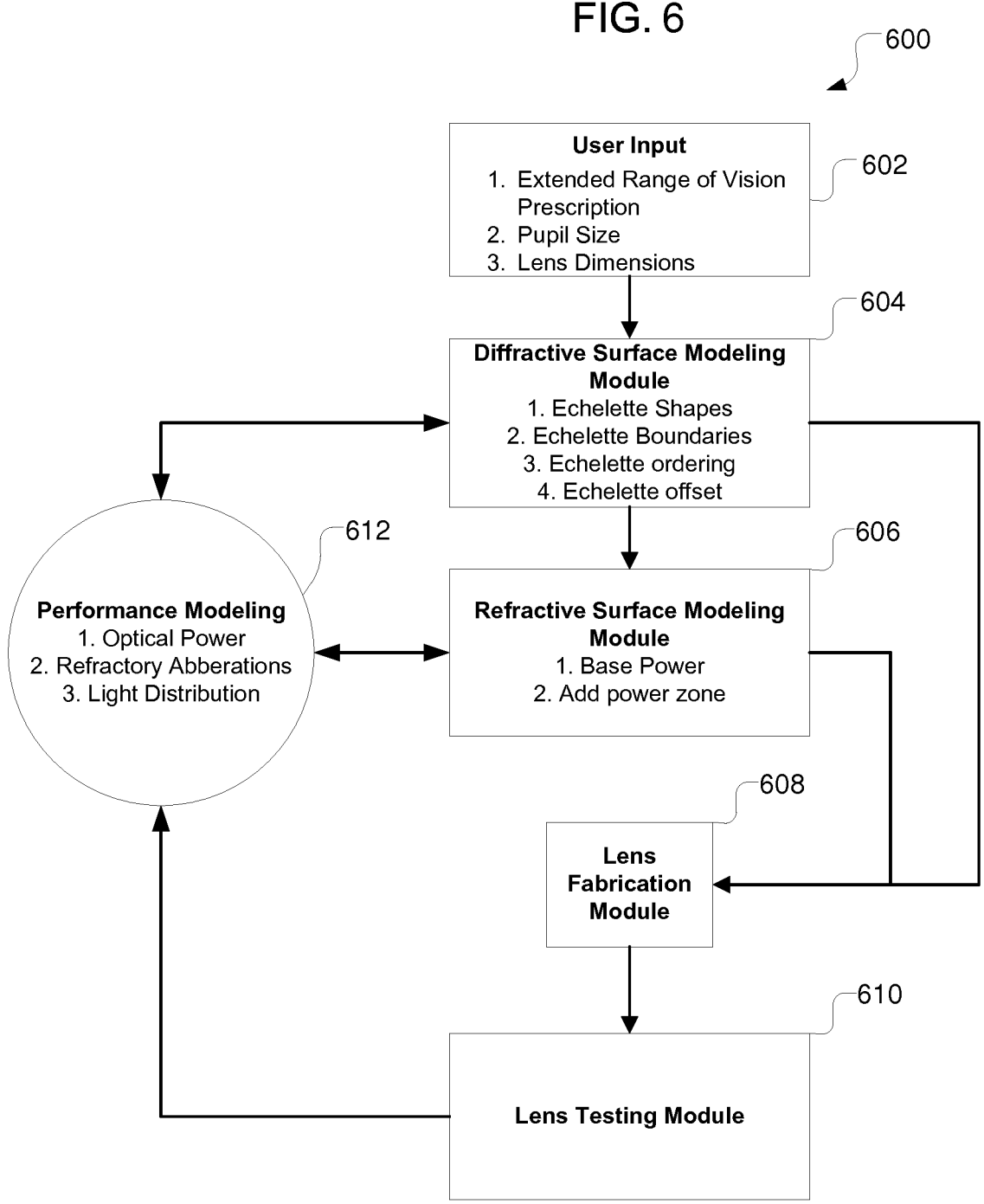
FIG. 6 is a simplified block diagram illustrating a system for generating a diffractive lens surface, in accordance with embodiments.

Systems and Methods for Determining Lens Shape:

FIG. 6 is a simplified block diagram illustrating a system 600 for generating an ophthalmic lens based on a user input.

The system 600 includes a user input module 602 configured to receive user input defining aspects of the user and of a lens. The input may accept an ophthalmic lens prescription for a patient eye. Aspects of a lens may include an extended range of vision prescription, anatomical dimensions like a pupil size performance, and lens dimensions, among other attributes. An extended range of vision prescription can include, for example, a preferred optical power or optical power profile for correcting far vision and an optical power or optical power profile for near vision. In some cases, an extended range of vision prescription can further include an optical power or optical power profile for correcting intermediate vision at two, or in some cases more than two intermediate foci, which may fall between the optical powers or ranges of optical powers described above. A pupil size performance can include a pupil radius of a patient and the visual field to be optimized. These parameters can also be related to patient's life style or profession, so that the design incorporates patient's visual needs as a function of the pupil size. Lens dimensions can include a preferred radius of the total lens, and may further include preferred thickness, or a preferred curvature of one or the other of the anterior surface and posterior surface of the lens.

A diffractive surface modeling module 604 can receive information about the desired lens from the user input module 602, and can determine aspects of a diffractive lens. The diffractive surface modeling module 604 may be multizonal and may be configured to determine aspects of a multizonal diffractive lens. The diffractive surface modeling module 604 may generate a diffractive profile based on the ophthalmic lens prescription. For example, the modeling module 604 can determine the shape of one or more echelettes of the diffractive profile of a diffractive multifocal lens, including the positioning, width, step height, and curvature needed to fulfill the target prescription for each of the echelettes, as well as the positioning of any subset of echelettes. The diffractive surface modeling module 604 can further determine the shapes of transition steps between echelettes. For example, transition steps may be smoothed or rounded to help mitigate optical aberrations caused by light passing through an abrupt transition. Such transition zone smoothing, which may be referred to as a low scatter profile, can provide for reductions in dysphotopsia by reducing the errant concentration of incident light behind the lens by the transition zones. By way of further example, echelette ordering, echelette offsets, and echelette boundaries may be adjusted to adjust the step heights between some adjacent echelettes. In particular, the diffractive surface modeling module can determine echelette offsets to set one or more step heights at echelette transitions to zero, or approximately zero, by these or similar methods. The generated diffractive profile may be any of the diffractive profiles disclosed in this application.

The diffractive surface modeling module 604 can be configured to generate performance criteria 612, e.g. via modeling optical properties in a virtual environment. Performance criteria can include the match of the optical power profile of the diffractive lens with the desired optical power profile based on the extended range of vision prescription. The performance criteria can also include the severity of diffractive aberrations caused by lens surface. In some cases, the diffractive surface modeling module 604 can provide a lens surface to a lens fabrication module for facilitating the production of a physical lens, which can be tested via a lens testing module 610 for empirically determining the performance criteria 612, so as to identify optical aberrations and imperfections not readily discerned via virtual modeling, and to permit iteration. The lens fabrication module may comprise a manufacturing assembly that may fabricate the ophthalmic lens based on the diffractive profile.

A refractive surface modeling module 606 can receive information from the user input 602 and diffractive surface modeling modules 604 in order to determine refractive aspects of the lens. For example, provided with an extended range of vision prescription and a set of diffractive powers that can be generated by a diffractive profile, the refractive surface modeling module 606 can provide a refractive geometry configured to provide a base power which, when combined with the diffractive surface, meets the requirements of the extended range of vision prescription. The refractive surface modeling module 606 can also generate performance criteria 612, and can contribute to providing a lens surface to a lens fabrication module 608 for facilitating the production of the physical lens.

Figure 7:
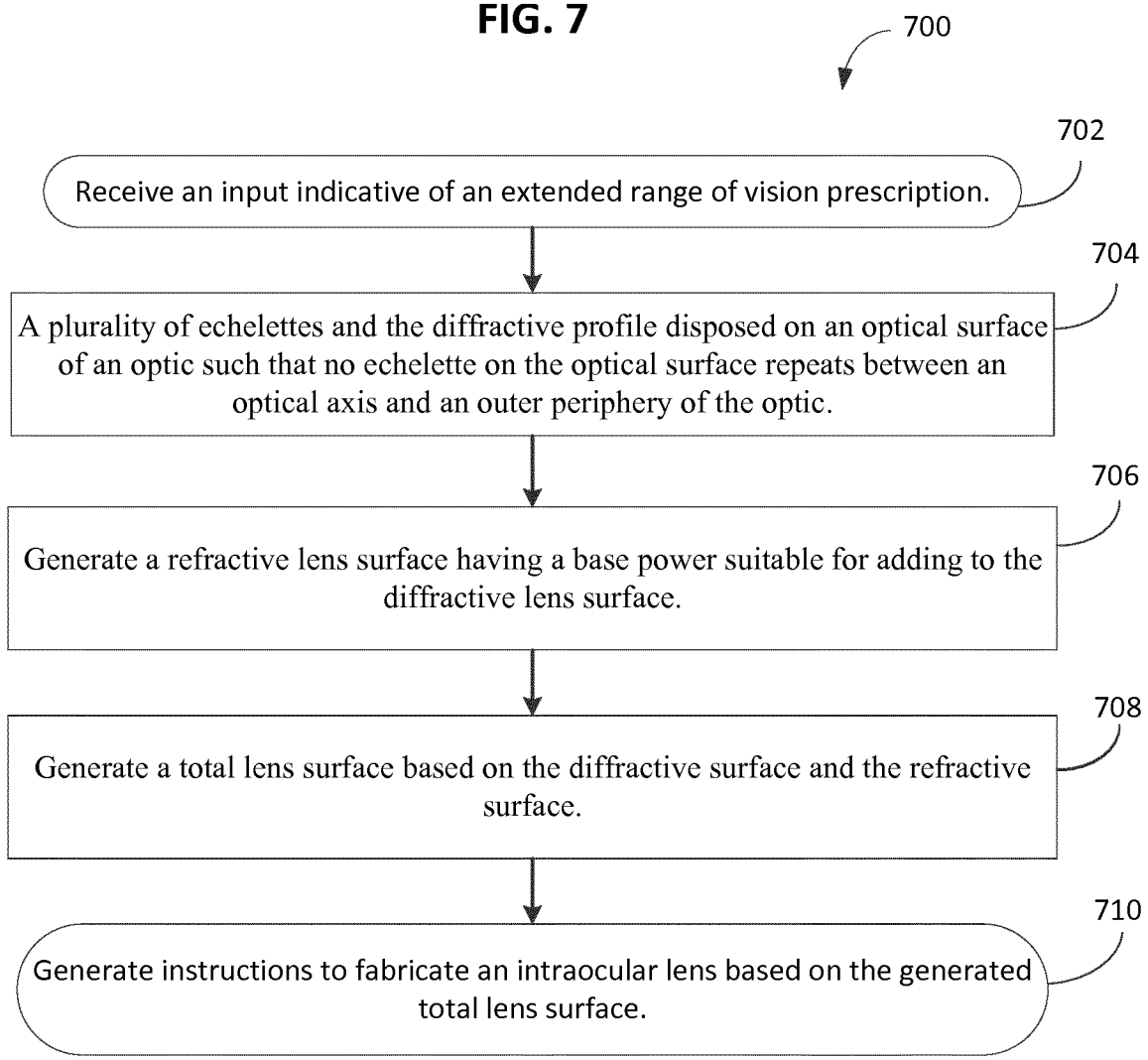
FIG. 7 illustrates an example process for generating a diffractive lens surface.

FIG. 7 is an example process 700 for generating a diffractive lens surface, in accordance with embodiments. The process 700 may be implemented in conjunction with, for example, the system 600 shown in FIG. 6. Some or all of the process 700 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 700 may include a method of designing an intraocular lens and may include receiving an input of an ophthalmic lens prescription for a patient eye, which may be an extended range of vision lens prescription (act 702). The input can include, e.g., a desired optical power profile for correcting impaired distance vision, a desired optical power profile for correcting impaired intermediate distance vision, a desired optical power profile for accommodating near vision, and any suitable combination of the above. Based on a desired optical power profile, a diffractive profile can be defined and generated. The generated diffractive profile may include a plurality of echelettes and the diffractive profile disposed on an optical surface of an optic such that no echelette on the optical surface repeats between an optical axis and an outer periphery of the optic (act 704).

The diffractive lens profile of the diffractive lens surface may be used in combination with a known refractive base power. To that end, a refractive lens surface may be generated having a base power that, in combination with the diffractive lens surface generated based on the diffractive profile, meets the extended range of vision lens prescription (act 706). A total lens surface can be generated based on both the refractive lens surface and the diffractive lens surface (act 708). The refractive lens surface can include a refractive lens curvature on the anterior surface of the lens, the posterior surface of the lens, or both. Instructions can be generated to fabricate an intraocular lens based on the generated total lens surface (act 710). A manufacturing assembly may fabricate the ophthalmic lens based on the instructions.

The methods herein are not limited to the examples of diffractive profiles discussed here, and may extend to any of the diffractive lens profiles and ophthalmic lenses disclosed in this application. For example, the diffractive profile that the diffractive lens surface is based on may include a plurality of echelettes disposed on an optical surface of an optic, and at least one of the plurality of echelettes may be connected to an adjacent echelette by a step height of zero. As another example, the diffractive profile that the diffractive lens surface is based on may include a plurality of echelettes. The diffractive profile may be disposed on the optical surface such that each echelette on the optical surface between the optical axis and the outer periphery of the optic has a profile in r-squared space that is different than a profile in r-squared space of any other echelette on the optical surface between the optical axis and the outer periphery of the optic. As another example, the diffractive profile that the diffractive lens surface is based on may include a plurality of echelettes and be disposed on an optical surface within a radially extending zone such that no echelette repeats within the radially extending zone. The radially extending zone may extend radially outward from the optical axis to the outer periphery of the optic.

Figure 8:
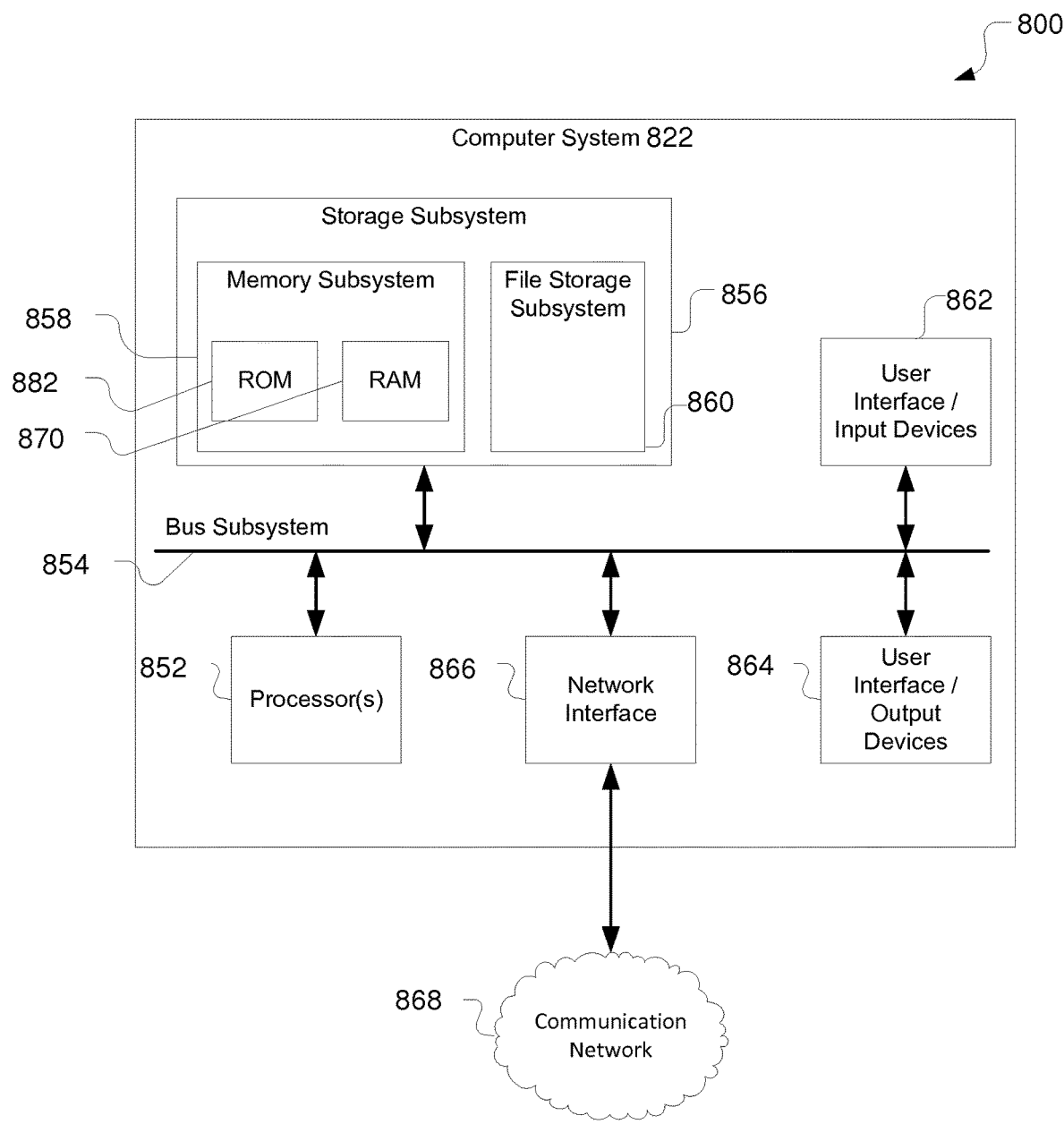
FIG. 8 illustrates an example computing environment for facilitating the systems and processes of FIGS. 6 and 7.

Computational Methods:

FIG. 8 is a simplified block diagram of an exemplary computing environment 800 that may be used by systems for generating the diffractive profiles and ophthalmic lenses of the present disclosure. Computer system 822 typically includes at least one processor 852 which may communicate with a number of peripheral devices via a bus subsystem 854. These peripheral devices may include a storage subsystem 856 comprising a memory subsystem 858 and a file storage subsystem 860, user interface input devices 862, user interface output devices 864, and a network interface subsystem 866. Network interface subsystem 866 provides an interface to outside networks 868 and/or other devices, such as the lens fabrication module 608 or lens testing module 610 of FIG. 6.

User interface input devices 862 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 862 will often be used to download a computer executable code from a tangible storage media embodying any of the methods of the present disclosure. In general, use of the term "input device" is intended to include a variety of conventional and proprietary devices and ways to input information into computer system 822.

User interface output devices 864 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 822 to a user.

Storage subsystem 856 can store the basic programming and data constructs that provide the functionality of the various embodiments of the present disclosure. For example, a database and modules implementing the functionality of the methods of the present disclosure, as described herein, may be stored in storage subsystem 856. These software modules are generally executed by processor 852. In a distributed environment, the software modules may be stored on a plurality of computer systems and executed by processors of the plurality of computer systems. Storage subsystem 856 typically comprises memory subsystem 858 and file storage subsystem 860. Memory subsystem 858 typically includes a number of memories including a main random access memory (RAM) 870 for storage of instructions and data during program execution and/or a read only member (ROM) 882.

Various computational methods discussed above, e.g. with respect to generating a lens surface, multizonal or not, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

What is claimed is:

1. An ophthalmic lens comprising:
an optic including a first surface and a second surface each disposed about an optical axis and extending radially outward from the optical axis to an outer periphery of the optic, the first surface facing opposite the second surface; and
a diffractive profile including a plurality of echelettes and disposed on the first surface such that each echelette on the first surface between the optical axis and the outer periphery of the optic has a slope in r-squared space that is different than a slope in r-squared space of any other echelette on the first surface between the optical axis and the outer periphery of the optic.

2. The ophthalmic lens of claim 1, wherein at least one of the plurality of echelettes has a step height of zero.

3. The ophthalmic lens of claim 1, wherein at least three of the plurality of echelettes have a step height of zero.

4. The ophthalmic lens of claim 1, wherein the plurality of echelettes includes at least five echelettes.

5. The ophthalmic lens of claim 1, wherein the plurality of echelettes includes at least twelve echelettes.

6. The ophthalmic lens of claim 1, wherein the plurality of echelettes includes at least thirty echelettes.

7. The ophthalmic lens of claim 1, wherein a first echelette of the plurality of echelettes has a step height that is greater than a step height of a second echelette of the plurality of echelettes.

8. The ophthalmic lens of claim 1, wherein a first echelette of the plurality of echelettes has a step offset that is greater than a step offset of a second echelette of the plurality of echelettes.

9. An ophthalmic lens comprising:
an optic having an optical axis, an outer periphery, and a first surface and a second surface disposed about the optical axis and facing opposite each other and extending radially outward from the optical axis to the outer periphery of the optic; and
a diffractive profile disposed on the first surface and including a plurality of echelettes, wherein:
at least one of the plurality of echelettes is connected to an adjacent echelette by a step height of zero, and wherein the at least one of the plurality of echelettes has a slope in r-squared space that is different than a slope in r-squared space of any other echelette on the first surface between the optical axis and the outer periphery of the optic.

10. The ophthalmic lens of claim 9, wherein at least three of the plurality of echelettes are connected to an adjacent echelette by a step height of zero.

11. The ophthalmic lens of claim 9, wherein at least six of the plurality of echelettes are connected to an adjacent echelette by a step height of zero.

12. The ophthalmic lens of claim 9, wherein the adjacent echelette has a slope in r-squared space that is different than a slope in r-squared space of any other echelette on the first surface between the optical axis and the outer periphery of the optic.

13. The ophthalmic lens of claim 12, wherein each of the plurality of echelettes has a slope in r-squared space that is different than a slope in r-squared space of any other echelette on the first surface between the optical axis and the outer periphery of the optic.

14. The ophthalmic lens of claim 13, wherein the plurality of echelettes includes at least thirty echelettes.

15. An ophthalmic lens comprising:
an optic including a first surface and a second surface each disposed about an optical axis and extending radially outward from the optical axis to an outer periphery of the optic, the first surface facing opposite the second surface and including a radially extending zone positioned between the optical axis and the outer periphery of the optic; and
a diffractive profile including a plurality of echelettes and disposed on the first surface within the radially extending zone such that each echelette within the radially extending zone has a slope in r-squared space that is different than a slope in r-squared space of any other echelette within the radially extending zone.

16. The ophthalmic lens of claim 15, wherein the radially extending zone extends radially outward from the optical axis to the outer periphery of the optic.

17. The ophthalmic lens of claim 16, wherein the plurality of echelettes includes at least five echelettes.

18. The ophthalmic lens of claim 15, wherein the radially extending zone extends radially outward from the optical axis to a radial distance of 1.5 millimeters.

19. The ophthalmic lens of claim 18, wherein the radially extending zone is a central zone, and the first surface includes a peripheral zone extending radially outward from the central zone; and the diffractive profile includes at least one echelette that repeats within the peripheral zone.

20. The ophthalmic lens of claim 15, wherein the radially extending zone extends radially outward from the optical axis to a radial distance of 2.5 millimeters.

21. A method of designing an intraocular lens, the method comprising:

defining a diffractive profile including:
a plurality of echelettes and the diffractive profile disposed on an optical surface of an optic such that each echelette on the optical surface between an optical axis and an outer periphery of the optic has a slope in r-squared space that is different than a slope in r-squared space of any other echelette of the plurality of echelettes; and generating a diffractive lens surface based on the diffractive profile.

22. The method of claim 21, wherein the plurality of echelettes includes at least five echelettes.

23. The method of claim 21, wherein the plurality of echelettes includes at least thirty echelettes.

24. The method of claim 21, wherein at least one of the plurality of echelettes has a step height of zero.

25. A method of designing an intraocular lens, the method comprising:

defining a diffractive profile including:
a plurality of echelettes disposed on an optical surface of an optic, and
at least one of the plurality of echelettes is connected to an adjacent echelette by a step height of zero, wherein the at least one of the plurality of echelettes has a slope in r-squared space that is different than a slope in r-squared space of any other echelette on the optical surface; and generating a diffractive lens surface based on the diffractive profile.

26. The method of claim 25, wherein at least three of the plurality of echelettes are connected to an adjacent echelette by a step height of zero.

27. The method of claim 25, wherein the optical surface extends radially outward from an optical axis to an outer periphery of the optic, and each of the plurality of echelettes has a slope in r-squared space that is different than a slope in r-squared space of any other echelette on the optical surface between the optical axis and the outer periphery of the optic.

28. A manufacturing system for making an ophthalmic lens, the system comprising:

an input that accepts an ophthalmic lens prescription for a patient eye;
a first module configured to generate a diffractive profile based on the ophthalmic lens prescription, wherein the diffractive profile includes:
a plurality of echelettes and the diffractive profile disposed on an optical surface of an optic such that each echelette on the optical surface has a slope in r-squared space that is different than a slope in r-squared space of any other echelette between an optical axis and an outer periphery of the optic; and
a manufacturing assembly that fabricates the ophthalmic lens based on the diffractive profile.

29. The system of claim 28, wherein the plurality of echelettes includes at least thirty echelettes.

30. The system of claim 28, wherein at least one of the plurality of echelettes has a step height of zero.

31. A manufacturing system for making an ophthalmic lens, the system comprising:

an input that accepts an ophthalmic lens prescription for a patient eye;
a first module configured to generate a diffractive profile based on the ophthalmic lens prescription, wherein the diffractive profile includes:
a plurality of echelettes disposed on an optical surface of an optic, and
at least one of the plurality of echelettes is connected to an adjacent echelette by a step height of zero, wherein the at least one of the plurality of echelettes has a slope in r-squared space that is different than a slope in r-squared space of any other echelette on the optical surface; and
a manufacturing assembly that fabricates the ophthalmic lens based on the diffractive profile.

32. The system of claim 31, wherein at least three of the plurality of echelettes are connected to an adjacent echelette by a step height of zero.

33. The system of claim 31, wherein the optical surface extends radially outward from an optical axis to an outer periphery of the optic, and each of the plurality of echelettes has a slope in r-squared space that is different than a slope in r-squared space of any other echelette on the optical surface between the optical axis and the outer periphery of the optic.

* * * * *